United States Patent [19]
Theoharides

[11] Patent Number: 6,020,305
[45] Date of Patent: *Feb. 1, 2000

[54] TREATMENT OF STRESS-INDUCED SKIN DISEASE BY CORTICOTROPIN RELEASING HORMONE ANTAGONISTS AND SKIN MAST CELL DEGRANULATION INHIBITORS

[75] Inventor: Theoharis C. Theoharides, Brookline, Mass.

[73] Assignee: Kos Pharmaceuticals, Inc., Miami, Fla.

[ * ] Notice: This patent issued on a continued prosecution application filed under 37 CFR 1.53(d), and is subject to the twenty year patent term provisions of 35 U.S.C. 154(a)(2).

[21] Appl. No.: 08/689,277

[22] Filed: Aug. 6, 1996

[51] Int. Cl.[7] .......................... A61K 37/00; A61K 31/35
[52] U.S. Cl. ................ 514/2; 514/456; 514/653
[58] Field of Search ................ 514/2, 456, 653

[56] References Cited

FOREIGN PATENT DOCUMENTS

WO 90/06104  6/1990  WIPO .

OTHER PUBLICATIONS

Shapiro et al. Pharmacotherapy 5(3): 156–170 (1985).
Webster et al. Endocrinology 137(12): 5747–5750 (1996).
Tauberg et al. Anesthesia Progress XXX(6): 199–200 (1983).
Koblenzer Psychodermatology 14(3): 447–455 (1996).

*Primary Examiner*—Zohreh Fay
*Attorney, Agent, or Firm*—Foley & Lardner

[57] ABSTRACT

A method of reducing or blocking a stress-related atopic skin disease such as exzema or uticaria in a subject comprising administering to the patient an agent that antagonizes CRH-induced activation of skin mast cells, the agent being used alone or together with a second agent that inhibits activation of skin mast cells. Such agents include compositions that reduce the production or secretion of CRH, neurotensin or somatostatin or an agent that inhibitos the physiological action of CRH, neurotensin or somostatin on skin mast cells. The effects of CRH on skin mast cells can also be inhibited by histamine-3 receptor antagonists and by inhibitors of the phosphorylation of skin mast cell moesin.

17 Claims, No Drawings

TREATMENT OF STRESS-INDUCED SKIN DISEASE BY CORTICOTROPIN RELEASING HORMONE ANTAGONISTS AND SKIN MAST CELL DEGRANULATION INHIBITORS

BACKGROUND OF THE INVENTION

The invention relates in general to treatment of atopic, stress related skin disease. In particular, the invention relates to effects of Corticotropin-Releasing Hormone ("CRH") on skin mast cells that result in various skin disorders, and the use of inhibitors and antagonists of CRH to treat such conditions.

CRH is a major regulator of the hypothalamic-pituitary-adrenal axis and principal coordinator of the stress response. While the neuroendocrine release of CRH results in anti-inflammatory effects through activation of the hypothalamic-pituitary-adrenal axis and the sympathetic nervous system, recent evidence suggests that CRH is also secreted peripherally and may have pro-inflammatory actions. Immunoreactive CRH (iCRH) has been localized to immune accessory cells in induced aseptic joint inflammation, in streptococcal arthritis, as well as experimental uveitis. CRH can be synthesized locally at inflammatory sites as evidenced by the presence of CRH mRNA in chronically inflamed synovia in rats or released by post-ganglionic sympathetic neurons and sensory afferent fibers. Immunocytochemistry has also verified the presence of iCRH in human tissues undergoing inflammatory processes.

Both iCRH and CRH mRNA have been demonstrated in rat and mouse spleen and thymus, as well as in human peripheral blood leukocytes, while mitogenic stimulation of human T lymphocytes results in synthesis of CRH. However, there is a discrepancy between the abundance of iCRH and the paucity of its mRNA at inflammatory sites in the early, acute phase of inflammation. The demonstration of CRH-like immunoreactivity in the dorsal horn of the spinal cord and dorsal root ganglia, as well as in sympathetic nerve cell bodies and sympathetic ganglia, support the hypothesis that the majority of iCRH in early inflammation is of nerve cell rather than immune cell origin. For purposes of the present invention, it is important that CRH and CRH-receptor mRNA have been identified in human skin (Slominski et al., *FEBS Letts.*, 374:113 (1995)).

CRH administration to humans or animals causes significant peripheral vasodilation manifested as increased blood flow and flushing. Immune CRH also appears to have pro-inflammatory actions as systemic administration of rabbit anti-CRH serum suppressed both the amount of exudate and inflammatory cell accumulation in induced inflammation (Karalis et al., *Science*, 254: 421(1991)), as well as the severity of experimentally-induced uveitis. Moreover, when this antiserum was administered prior to acute psychological stress, it blocked the resultant activation of dura mast cells (Theoharides et al., *Endocrinol.* 136:5745 (1995). Analogous to the marked appearance of iCRH, there is activation and proliferation of mast cells at inflammatory sites.

Mast cells are located in the perivascular area close to peripheral nerves and, when activated by nerve stimulation or sensory neuropeptides, they secrete potent vasoactive and proinflammatory mediators including histamine, cytokines, prostanoids and proteases. In fact, tumor necrosis factor (TNF) released from skin mast cells induces both vasodilation and expression of endothelial adhesion molecule-1, while skin mast cell activation by substance P (SP) leads to granulocyte infiltration.

In the light of this background, it is an object of this invention to discover whether iCRH may be involved in the pathophysiology of certain skin conditions that are exacerbated by stress, such as eczema and urticaria. CRH could interact with the immune and the nervous systems and contribute to inflammation, possibly through activation of mast cells. Such a functional relation between central CRH, iCRH, neurons and mast cells could be important in normal physiology, in the context of hypersensitivity reactions, and in neuroimmunoendocrine or inflammatory syndromes. A further object of this invention was to test this hypothesis by examining the ability of CRH and stress to activate skin mast cells. It is an additional object of this invention to provide treatments that block or inhibit the effects of CRH on mast cell related skin disorders.

SUMMARY OF THE INVENTION

These objects have been achieved by the discovery that CRH causes activation of skin mast cells and skin vasodilation, an effect that is reproduced by acute psychological stress due to immobilization. The invention comprises treatment of stress-exacerbated skin disorders in a subject by the administration of substances that antagonize the physiological effects of CRH on skin mast cells.

In one embodiment of the invention, anti-CRH antibodies are administered to a subject to treat CRH-related skin disorders.

In another embodiment, blocking anti-CRH receptor antibodies or anti-receptor antagonists are administered to a subject to treat CRH-related skin disorders.

In still another embodiment, antagonists of neurotensin ("NT") and NT receptors are administered to block the potentiating effect of NT on the action of CRH on skin mast cells.

In yet another embodiment, pharmaceutical inhibitors of skin mast cell degranulation are administered either alone or with the CRH and NT antagonists mentioned above.

In a yet further embodiment, combinations of CRH antagonists and skin mast cell degranulation inhibitors are used to treat atopic skin disorders.

These and other embodiments will become apparent by reference to the specification and appended claims.

DETAILED DESCRIPTION OF THE PREFERRED EMBODIMENTS

This invention is based on the present discovery that stress-related skin disorders such as eczema and uticaria in a human subject can be treated by administering to the subject an antagonist of the physiological actions of CRH on skin mast cells. The term "antagonist" is used herein to include agents that inhibit or block the synthesis or release of CRH from tissue sources or that reduce the physiological effects of CRH as an activator of skin mast cell degranulation.

The aforementioned CRH antagonists include compositions that directly or indirectly reduce CRH release from neurons or other sources or inhibit CRH actions on skin mast cells. Such antagonists include an anti-CRH antibody or a structural analogue of CRH, which includes amino acid substitutions and derivatization. The antagonists may be agents that block the activity of CRH on skin mast cell receptors, such as anti-CRH receptor antibodies. The antagonists may be compounds that block or antagonize the actions of biochemicals that mediate or promote CRH actions, such as an anti-neurotensin ("NT") antibody or an NT receptor antagonist. The antagonist may be an agent that inhibits skin mast cell activation, such as a bichromone (e.g.

cromolyn (disodium cromoglycate)), a flavonoid (kaempferol), other compounds that stimulate the phosphorylation of the 78 kDa mast cell moesin (see pending U.S. Ser. No. 08/631,184), a piperazine (e.g., hydroxyzine), or a histamine-3 receptor agonist ($N^{\alpha}$-methyl histamine, Calbiochem/Novabiochem, La Jolla, Calif.).

As noted above, inhibition of the effect of CRH in the development of atopic skin disorders may be achieved by treating a subject with an an antagonist of the production or release of CRH from neurons and other sites of origin, by inhibiting the binding of CRH to mast cell CRH receptors, and by inhibiting the physiological action(s) of CRH on mast cells (for example, by an antiserum to NT or an anti-NT receptor antibody administered parenterally or topically). Although applicant need not be bound by any particular theory of mechanism of action, it is likely that the anti-CRH antibody by binding to CRH, and an anti-CRH receptor antibody or CRH receptor blocker by blocking the binding of CRH to its physiological receptor(s) on skin mast cells, thereby inhibits or blocks CRH activation of skin mast cells.

Other CRH antagonists are expected to have the same beneficial effects as the anti-CRH antibody, and therefore are within the scope of this invention. Examples include a CRH receptor antagonist such as the CRH peptide analogue D-Phe$^{12}$, Nle$^{32, 21}$, Ala$^{38}$ hCRH (12–41)NH2 (Neurocrine Biochemicals, Inc., cat. no. 1P-36-41, MW 3474.1), and Pfizer's non-peptide CRH analog CP-154,526-1 that will compete with CRH for binding to CRH receptor(s) on mast cells. Other examples include inhibitors of CRH secretion such as agents that activate histamine-3 receptors.

Anti-CRH polyclonal serum may be prepared by routine immunization of rabbits with commercially available recombinant CRH (rCRH) (Sigma Chem. Co., St. Louis, Mo.) according to Karalis et al., *Science*, 254:421 (1991), which is incorporated herein by reference in its entirety, or obtained from Phoenix Pharmaceuticals, California. A rabbit anti-NT receptor serum can be purchased from Sanofi Research, Toulouse, France, which is also the source of the nonpeptide NT receptor antagonist SR 48692.

Anti-CRH and anti-NT polyclonal or monoclonal antibodies or other inhibitors may be administered parenterally, orally, sublingually, topically or transdermally to subjects in a pharmaceutically acceptable carrier such as those described in Remington's Pharmaceutical Sciences, Mack Publishing Co., Easton, Pa., 1988, which is incorporated herein by reference. For parenteral use, concentrations of about 0.1 to 10 mg protein/ml for anti-CRH and anti-NT sera, and at a concentration of 1 to 1000 nM for the NT receptor antagonist SR 48692 or CRH receptor antagonists shown above may be used. Cromolyn (Fisons, Inc.) in a pharmaceutically acceptable vehicle may be administered to patients in two 100 mg capsules before meals and at bedtime. Transdermal injections or patches may also be used. Physicians of skill in this art will, without undue experimentation, select the proper inhibitors and the appropriate dosages and routes of administration for the particular clinical picture.

Although skin mast cell activation can be determined histologically by light or electron microscopy, or by dye extravasation, as described below, it can also be determined by assaying peripheral blood by routine methods for the appearance of the products of activation, such as histamine, its metabolite N-methyl-histamine, or the proteolytic enzyme tryptase as described in Roznecki et al., *Ann. Neurol.* 37:63 (1995) which is incorporated herein by reference in its entirety.

The CRH receptor cDNA has been cloned from a variety of animal species and organs. Perris et al., *PNAS USA*, 92:2968 (1995). CRH receptors range in size from 415 to 431 amino acid residues with 68% homology between rodent and human molecules. The exact type of skin cells expressing CRH receptors may, therefore, be determined by in situ hybridization and reverse transcriptase PCR (Slominski et al., *FEBS Letts.* 374:113 (1995)).

The examples that follow are designed to exemplify the invention and are not intended to limit the scope of the invention, which is described in the specification and appended claims.

The following materials and methods were employed in the examples described below:

1. For extravasation experiments, male Sprague/Dawley rats, each weighing approximately 350 g (Taconic Farms, Germantown, N.Y.), were anesthetized with a single intraperitoneal injection of 0.5 ml ketamine and 0.5 ml xylazine (20 mg/ml each) and then injected intravenously with 0.1 ml of 1% Evan's blue 60 min prior to treatment.

2. Drugs tested by intradermal injection in a volume of 0.1 ml include: a) 0.1 µg/ml of the mast cell specific secretagogue, compound 48/80 (C48/80), b) $10^{-5}$ M substance P (Sigma), c) various concentrations of CRH (Sigma, St. Louis), d) the CRH receptor antagonist [D-Phe$^{12}$Nle$^{21,38}$, Ala$^{32}$]rCRH(12–41), e) the inactive free acid form of recombinant/human CRH (r/h CRH—OH), both obtained from Neurocrine Biosciences, CA, f) somatostatin (somatotropin release inhibitory factor, SRIF Bachem, Calif.), g) diphenylhydramine (Sigma), H) terfenadine (Sigma), i) hydroxyzine (UCB, Belgium) and j) the antiserum to the 78 kDa portion of the Tumor Necrosis Factor receptor (Harland Serolab, Ltd., Crawley Down, Sussex, England), in normal saline using a tuberculin syringe.

3. The pretreatment solution, when appropriate, was drawn first in the syringe followed by CRH from which it was separated by an air bubble. The pretreatment solution was injected first and was allowed to remain in the skin for 1 min; the needle was then changed, the air bubble ejected and CRH was injected and allowed to stay in the skin for 5 min. The animal was then killed by asphyxiation over $CO_2$ vapor and decapitated; the skin was removed, turned over and photographed.

4. In other rats, the skin was rapidly removed at the end of the injection period and was fixed in 4% paraformaldehyde for light microscopy (Theoharides et al., *Int. Arch. Allergy Immunol.* 102:352 (1993)), which is incorporated herein by reference in its entirety. The tissue was then frozen and thin sections (7 µ) were cut using a cryostat (Jung CM 3000, Leica, Luc. Deerfield, Ill.). The sections were stained with acidified (pH<2.5) toluidine blue (Sigma, St. Louis) and all mast cells were counted, by two different researchers blinded to the experimental conditions, at 400× magnification using a Diaphot inverted Nikon microscope (Don Santo, Mass.).

5. For depletion of neuropeptide-containing sensory nerves, one entire litter of rats was injected with capsaicin within two days of birth and the males were used five weeks later as described before (Dimitriaou et al., *Neuroscience* 44: 97 (1991), which is incorporated by reference herein in its entirety. The effectiveness of this procedure was confirmed by immunocytochemistry (Dimitraou 1991 above}, which showed that there were no Substance P-positive cells or nerve processes in the skin of capsaicin-treated rats.

EXAMPLE 1

CRH and Skin Vascular Permebility

CRH induced marked increases in skin vascular permeability, as evidenced by dye extravasation, an effect which was more pronounced than that obtained by an equimolar concentration of the mast cell secretagogue C48/80 or SP (Table 1).

EXAMPLE 2

CRH and Skin Mast Cell Activation

The CRH effect on skin mast cell activation was confirmed by morphological evidence of secretion as judged by granule content extrusion and loss of cellular staining in the skin samples from the injection site. Activation was observed in about 45% of the mast cells at skin sites treated with $10^{-4}$ M CRH (3 rats, n=841), as compared to 28% (3 rats, n=750)(p<0.05) of the mast cells from control sites (Table 1).

EXAMPLE 3

Ultrastructural Analysis of CRH-treated Skin Mast Cells

Ultrastructural observations of mast cells from CRH-injected sites had obvious sign of activation as evidenced by loss of the electron dense content of mast cell secretory granules. The effect of CRH on both vasodilation and mast cell activation was dose-dependent from $10^{-4}$ M–$10^{-8}$ M (Table 1).

EXAMPLE 4

Effect of CRH Receptor Antagonist

The peptide CRH-receptor antagonist [D-phe$^{12}$, Nle$^{21,38,}$ Ala$^{32}$]rCRH(12–41) did not block the effect of CRH, but at $10^{-4}$ M mimicked (25% activation) the effect of CRH although it was less potent both as measured by plasma extravasation and mast cell degranulation (Table 1). This antagonist ($10^{-4}$ M) could not inhibit dye extravasation even when CRH was used at $10^{-6}$ M (Table 3).

The inactive free acid analogue of CRH, r/h CRH—OH, however, produced no significant effect on mast cell degranulation (Table 1) suggesting that these pro-inflammatory actions of CRH are mediated by specific membrane receptors recognizing the amidated C terminal part of natural CRH.

EXAMPLE 5

Effect of Somatostatin and CRH on Extravasation

Somatotropin is a general anti-secretory polypeptide hormone. Pretreatment of the injection site with somatostatin ($10^{-4}$ M) before injecting CRH ($10^{-4}$ M) resulted in more dye extravasation than CRH alone (Table 2). In fact, somatostatin alone caused significant fluid extravasation which was as strong as that seen with CRH and was still apparent at $10^{-12}$ M (Table 4).

EXAMPLE 6

Effect of Histamine-1 Receptor Antagonist on CRH Extravasation

While pretreatment with the histamine-1 receptor antagonist diphenhydramine ($10^{-4}$ M) suppressed plasma extravasation at lower concentrations (<$10^{-8}$ M) of CRH, this effect was only partially inhibited at higher concentrations of (>$10^{-6}$ M) CRH (Table 2). Pretreatment with the non-sedating piperidine H-1 receptor antagonist terfenadine ($10^{-4}$ M) reduced the CRH effect slightly (Table 2), while pretreatment with the piperazine histamine-1 receptor antagonist hydroxyzine ($10^{-4}$ M) and the tricyclic antidepressant doxepin ($10^{-4}$M) blocked the CRH effect entirely (Table 2). These results suggest that mast cell release of histamine is a primary mechanism whereby CRH induces plasma extravasation.

EXAMPLE 7

Effect of Sensory Nerve Termini Destruction on CRH Effects.

In animals that had been treated neonatally with capsaicin to destroy neuropeptide-containing sensory nerve termini, mast cell activation by CRH ($10^{-4}$ M) was unaffected, indicating that its action was not due to neuropeptides such as Substance P.

EXAMPLE 8

Comparison of Mast Cells From Different Tissues

In order to ascertain whether CRH affects mast cells directly, the effects of CRH on purified rat peritoneal and pleural mast cells were compared to the effects of C48/80 and Substance P. CRH was largely ineffective on peritoneal mast cells, but induced histamine release from pleural mast cells in a dose-dependent manner which, like Substance P, required the absence of extracellular calcium ions (Table 5). Comparison of

EXAMPLE 9

Effect of Psychological Stress on Skin Mast Cells

Acute psychological stress due to immobilization of the test animals also activated skin mast cells, an effect blocked by pretreatment with anti-serum to CRH.

EXAMPLE 10

Identification of CRH-Positive Nerve Endings in Skin

Occasional CRH-positive nerve endings were identified in human skin using a polyclonal anti-CRH serum. Human skin is known to express mRNA for CRH and CRH receptor (Slominski, 1995 above). Additionally, human mast cells grown in culture were shown with polymerase chain reaction to contain message for the receptor (Webster et al., *Endocrin. Soc. Abs.* 77:669 (1995)).

Summary

These results clearly demonstrate that CRH induces rat skin mast cell activation which results in fluid extravasation. They further show that this activation is due to a direct effect of CRH on mast cells without any involvement of at least sensory neuropeptides. It is concluded that the skin mast cell is a target of iCRH. Our hypothesis is that CRH released from peripheral sensory afferent and/or postganglionic sympathetic nerves acts on local mast cells and other resident cells to elicit pro-inflammatory responses. The inflammatory mediators released could further stimulate mast cells, recruit circulating immune cells to the inflammatory site, activate local immune accessory cells and act on the nerve endings to release more inflammatory peptides. This could be of particular importance in inflammatory states triggered by acute stress, such as uticaria or eczema, in which activation of the sympathetic system and local secretion of CRH could lead to mast cell degranulation and initiation of a new episode or exacerbation of chronic disease.

The present results may help explain the pathophysiology of certain neuroinflammatory disorders, such as eczema, pruritus and urticaria, that are exacerbated by stress. Novel non-peptide CRH-receptor antagonists or other molecules that could interfere with CRH-induced skin mast cell degranulation may be useful for the treatment of such conditions

TABLE 1

Skin Mast Cell Activation by CRH

| Conditions (n = 3 rats) | Dye Extravasation (color intensity) | Total MC | Mast Cell Degranulation* (% total) Deg. MC | % total deg. |
|---|---|---|---|---|
| Normal saline | − | 750 | 206 | 28 |
| C48/80 (0.5 μg/ml) | +++ | 841 | 375 | 45 |
| CRH-α ($10^{-4}$ M) | + | 112 | 28 | 25 |
| CRH-OH ($10^{-4}$ M) | − | 144 | 13 | 9 |
| CRH ($10^{-4}$ M) | ++++ | 902 | 426 | 49$ |
| CRH ($10^{-5}$ M) | +++ | 915 | 327 | 37 |
| CRH ($10^{-6}$ M) | ++ | 810 | 331 | 42 |
| CRH ($10^{-7}$ M) | ++ | 1008 | 329 | 37 |
| CRH ($10^{-8}$ M) | ++ | 790 | 254 | 32 |
| CRH ($10^{-9}$ M) | + | 725 | 202 | 28 |
| CRH ($10^{-10}$ M) | ± | 880 | 239 | 26 |

*3 sections were examined from each of four blocks from each rat.
$p < 0.05$ compared to normal saline or CRH-OH, an inactive form of CRH.

TABLE 2

Effect of Drugs on Skin Mast Cell Activation by CRH*

| Conditions (n = 3) | Dye Extravasation (color intensity) |
|---|---|
| Normal saline | − |
| C48/80 (0.5 μg/ml) | +++ |
| CRH | +++ |
| TNF receptor blocker + CRH | +++ |
| Diphenhydramine ($10^{-4}$ M) + CRH | + |
| Doxepin ($10^{-4}$ M) + CRH | − |
| Hydroxyzine ($10^{-4}$ M) + CRH | − |
| Terfenadine ($10^{-4}$ M) + CRH | ++ |
| Somatostatin ($10^{-4}$ M) + CRH | ++++ |

*used at $10^{-4}$ M
ƒ pretreatment with drug for 5 mins.

TABLE 3

Effect of CRHα on Skin Mast Cells*

| CRH α concentration | Dye Extravasation |
|---|---|
| $10^{-4}$ M | +++ |
| $10^{-5}$ M | ++ |
| $10^{-6}$ M | ++ |
| $10^{-7}$ M | ± |
| $10^{-8}$ M | − |
| $10^{-9}$ M | − |
| $10^{-10}$ M | − |

*n = 3 rats

TABLE 4

Effect of Somatostatin on Skin Mast Cells*

| Somatostatin, concentration | Dye Extravasation |
|---|---|
| $10^{-4}$ M | +++ |
| $10^{-5}$ M | ++ |
| $10^{-6}$ M | ++ |
| $10^{-7}$ M | ++ |
| $10^{-8}$ M | + |
| $10^{-9}$ M | ± |
| $10^{-10}$ M | ± |

*n = 3 rats

TABLE 5

Effect of CRH on Purified Mast Cells

| | Histamine Release (% total) | | | |
|---|---|---|---|---|
| | Pleural | | Peritoneal | |
| Conditions | + Calcium | − Calcium | + Calcium | − Calcium |
| Locke's Solution | 2.205 | 4.478 | 2.0 | 4.9 |
| C48/80 ($10^{-4}$ M) | 86.045 | 67.12 | NT | NT |
| C48/80 ($10^{-5}$ M) | 75.552 | 61.059 | NT | NT |
| C48/80 ($10^{-6}$ M) | 47.537 | 45.203 | 64.2 | NT |
| SP ($10^{-4}$ M) | 49.346 | 54.591 | NT | NT |
| SP ($10^{-5}$ M) | 22.919 | 28.871 | NT | 39.5 |
| SP ($10^{-6}$ M) | 2.088 | 8.538 | NT | NT |
| CRH ($10^{-4}$ M) | 22.06 | 34.244 | 6.3 | 25.5 |
| CRH ($10^{-5}$ M) | 2.102 | 8.579 | 1.9 | 6.9 |
| CRH ($10^{-6}$ M) | 1.411 | 4.253 | 2.0 | 4.9 |

NT = not tested

What is claimed is:

1. A method for reducing or blocking atopic skin disorders in a subject, comprising the step of administering to said subject an effective amount of an antagonist of the activation of skin mast cells by CRH, wherein said antagonist is selected from the group consisting of anti-CRH antibody, competitive and non-competitive inhibitors of the binding of CRH to skin mast cell CRH receptors, agents that reduce the production or release of CRH in the skin of said subject, inhibitors of the action of neurotensin on skin mast cells, and agents that reduce the production or release of neurotensin.

2. The method of claim 1, wherein said antagonist is an anti-CRH antibody.

3. The method of claim 1, wherein said antagonist is a competitive or non-competitive inhibitor of the binding of CRH to skin mast cell CRH receptors.

4. The method of claim 1, wherein said antagonist reduces the production or release of CRH in the skin of said subject.

5. The method of claim 1, wherein said antagonist is an inhibitor of the action of neurotensin on skin mast cells.

6. The method of claim 5, wherein said antagonist reduces the production or release of neurotensin in the skin of said subject.

7. The method of claim 1, further comprising administering a second inhibitor along with said CRH antagonist, wherein said second inhibitor is either an inhibitor of mast cell degranulation or an antagonist of a histamine receptor.

8. The method of claim 7, wherein said second inhibitor is a histamine-3 receptor agonist.

9. The method of claim 7, wherein said said second inhibitor is a piperazine compound.

10. The method of claim 9, wherein said piperazine compound is hydroxyzine or an analogue thereof.

11. The method of claim 7, wherein said second inhibitor is an agent that stimulates the phosphorylation of at least one serine or threonine residue in skin mast cell moesin.

12. The method of claim 11, wherein said agent is a bichromone.

13. The method of claim 12, wherein said bichromone is cromolyn or an analogue thereof.

14. The method of claim 11, wherein said agent is a flavonoid.

15. The method of claim 14, wherein said flavonoid is kaempferol.

16. The method of claim 1, wherein said antagonist is an inhibitor of the production of somatostatin or action of somatostatin on skin mast cells.

17. The method of claim 1 or claim 7, wherein said antagonist or said second inhibitor or both in a pharmaceutically acceptable vehicle is administered to said subject by a route selected from the group consisting of parenteral, oral, sublingual, topical and transdermal.

* * * * *